United States Patent [19]

Edwards et al.

[11] Patent Number: 5,624,439
[45] Date of Patent: Apr. 29, 1997

[54] METHOD AND APPARATUS FOR TREATMENT OF AIR WAY OBSTRUCTIONS

[75] Inventors: Stuart D. Edwards, Los Altos; Edward J. Gough, San Carlos; David Douglass, Woodside, all of Calif.

[73] Assignee: Somnus Medical Technologies, Inc., Sunnyvale, Calif.

[21] Appl. No.: 516,779

[22] Filed: Aug. 18, 1995

[51] Int. Cl.$^6$ .................................................. A61B 1/24
[52] U.S. Cl. ........................... 606/45; 606/32; 606/41; 128/639; 128/848; 128/860
[58] Field of Search .................. 606/32, 41, 45–48; 128/639, 642, 848, 859–861

[56] References Cited

U.S. PATENT DOCUMENTS

| | | | |
|---|---|---|---|
| 1,798,902 | 3/1931 | Raney | 606/45 |
| 4,196,724 | 4/1980 | Wirt et al. | 128/860 |
| 5,046,512 | 9/1991 | Murchie | 128/848 |
| 5,316,020 | 5/1994 | Truffer | 128/848 |
| 5,365,945 | 11/1994 | Halstrom | 128/848 |
| 5,423,812 | 6/1995 | Ellman et al. | 606/45 |

*Primary Examiner*—Angela D. Sykes
*Assistant Examiner*—Stephen Huang
*Attorney, Agent, or Firm*—Wilson Sonsini Goodrich & Rosati

[57] ABSTRACT

An apparatus for treating air way obstructions, includes a first arm including a proximal end and a distal end, the first arm distal end is inserted into the throat and positioned adjacent to a back surface of the tongue. A second arm has a proximal end and a distal end. The second arm is positioned under the jaw. A coupling member couples the first arm with the second arm, permitting rotational movement of each arm about a longitudinal axis of the coupling member. A plurality of RF electrodes are positioned in the first arm. The plurality of RF electrodes are advanced into the back of the tongue and retracted out of the tongue and into the first arm, ablating a selected area of the back of the tongue.

27 Claims, 8 Drawing Sheets

METHOD AND APPARATUS FOR TREATMENT OF AIR WAY OBSTRUCTIONS

CROSS-REFERENCE TO RELATED APPLICATIONS

This application cross-references U.S. patent application No. 08/516,781, (Attorney Reference No. VCAR 1012 CIP1), filed Aug. 18, 1995, entitled "Ablation Apparatus and System for Removal of Soft Palate Tissue", having named inventors Stuart D. Edwards, Edward J. Gough and David L. Douglas, which is a continuation-in-part of U.S. application No. 08/239,658, (Attorney Reference No. VCAR 1012), filed May 9, 1994 entitled "Method for Reducing Snoring by RF Ablation of the Uvula", both applications are assigned to the assignee of the instant application and are herein incorporated by reference.

BACKGROUND OF THE INVENTION

1. Field of the Invention

This invention relates to a method and apparatus for maintaining upper airway patency in human patients, and more particularly to a method and apparatus which utilizes RF energy to ablate selected sections of the tongue and other structures without damage to nerve systems.

2. Description of Related Art

Sleep-apnea syndrome is a medical condition characterized by daytime hypersomnolence, morning armaches, intellectual deterioration, cardiac arrhythmias, snoring and thrashing during sleep. It is caused by frequent episodes of apnea during the patient's sleep. The syndrome is classically subdivided into two types. One type, termed "central sleep apnea syndrome", is characterized by repeated loss of respiratory effort. The second type, termed obstructive sleep apnea syndrome, is characterized by repeated apneic episodes during sleep resulting from obstruction of the patient's upper airway or that portion of the patient's respiratory tract which is cephalad to, and does not include, the larynx.

Treatment thus far includes various medical, surgical and physical measures. Medical measures include the use of medications such as protriptyline, medroxyprogesterone, acetazolamide, theophylline, nicotine and other medications in addition to avoidance of central nervous system depressants such as sedatives or alcohol. The medical measures above are sometimes helpful but are rarely completely effective. Further, the medications frequently have undesirable side effects.

Surgical interventions have included uvulopalatopharyngoplasty, tonsillectomy, surgery to correct severe retrognathia and tracheostomy. These procedures may be effective but the risk of surgery in these patients can be prohibitive and the procedures are often unacceptable to the patients.

Physical measures have included weight loss, nasopharygeal airways, nasal CPAP and various tongue retaining devices used nocturnally. These measures may be partially effective but are cumbersome, uncomfortable and patients often will not continue to use these for prolonged periods of time. Weight loss may be effective but is rarely achieved by these patients.

In patients with central sleep apnea syndrome, phrenic nerve or diaphragmatic pacing has been used. Phrenic nerve or diaphragmatic pacing includes the use of electrical stimulation to regulate and control the patient's diaphragm which is innervated bilaterally by the phrenic nerves to assist or support ventilation. This pacing is disclosed in *Direct Diaphragm Stimulation* by J. Mugica et al. PACE vol. Jan. 10–Feb. 1987, Part II, *Preliminary Test of a Muscular Diaphragm Pacing System on Human Patients* by J. Mugica et al. from Neurostimulation: An Overview 1985 pp. 263–279 and *Electrical Activation of Respiration* by Nochomovitez IEEE Eng. in Medicine and Biology; June, 1993.

However, it was found that many of these patients also have some degree of obstructive sleep apnea which worsens when the inspiratory force is augmented by the pacer. The ventilation induced by the activation of the diaphragm also collapses the upper airway upon inspiration and draws the patient's tongue anteriorly down the throat chocking the patient. These patients then require tracheostomies for adequate treatment.

A physiological laryngeal pacemaker as described in *Physiological Laryngeal Pacemaker* by F. Kaneko et al. from Trans Am Soc Artif Intern Organs 1985 senses volume displaced by the lungs and stimulates the appropriate nerve to open the patient's glottis to treat dyspnea. This apparatus is not effective for treatment of sleep apnea. The apparatus produces a signal proportional in the displaced air volume of the lungs and thereby the signal produced is too late to be used as an indicator for the treatment of sleep apnea. There is often no displaced air volume in sleep apnea due to obstruction.

One measure that is effective in obstructive sleep apnea is tracheostomy. However, this surgical intervention carries considerable morbidity and is aesthetically unacceptable to many patients. Other surgical procedures include pulling the tongue as forward as possible and surgically cutting and removing sections of the tongue and other structures which can close off the upper airway passage.

There is a need for an apparatus to treat air obstruction disorders that removes portions of the tongue without major surgical intervention.

SUMMARY OF THE INVENTION

Accordingly, an object of the invention is to provide an RF ablation apparatus that ablates selected portions of the tongue without major surgical intervention.

Another object of the invention is to provide an RF ablation apparatus that ablates selected portions of the tongue which compresses between the back of the tongue and the lower portion of the jaw.

A further object of the invention is to provide an RF ablation apparatus to treat air passage disorders which includes a first arm that extends into the throat, and a second arm that adds a compression force at the lower section of the jaw.

Yet another object of the present invention is to provide an RF ablation apparatus to treat sleep apnea which includes first and second arms positioned at the back of the tongue, and underneath the jaw, with each arm including a plurality of retractable electrodes that are introduced into selected sections of the tongue, effecting selected ablation of the tongue.

These and other objects of the invention are achieved in an apparatus for treating air way obstructions. The apparatus includes a first arm including a proximal end and a distal end. The first arm distal end is inserted into the throat and positioned adjacent to a back surface of the tongue. A second arm has a proximal end and a distal end. The second arm is positioned under the jaw. A coupling member couples the first arm with the second arm, permitting rotational movement of each arm about a longitudinal axis of the coupling member. A plurality of RF electrodes are positioned in the first arm. The plurality of RF electrodes are advanced into the back of the tongue and retracted out of the tongue and into the first arm, ablating a selected area of the back of the tongue.

In another embodiment the apparatus for treating air way obstructions includes one or more sensors positioned at an interior or an exterior of the RF electrodes, or on an interior or exterior surface of the first arm distal end. The sensors detect impedance or temperature. A sensor feedback apparatus is coupled to the sensors and maintains a tissue adjacent to the RF electrodes at a desired temperature.

An insulation sleeve surrounds each RF electrode, and is capable of movement along a longitudinal length of the RF electrode. The plurality of RF electrodes can also be positioned in the second arm in order to ablate selected sections of the underside of the tongue. One or more lumens are positioned in the first arm to introduce a variety of mediums including but not limited to oxygen or an anesthetic. Further, a visualization device is coupled to a proximal end of the apparatus.

DETAILED DESCRIPTION

Figure 1:
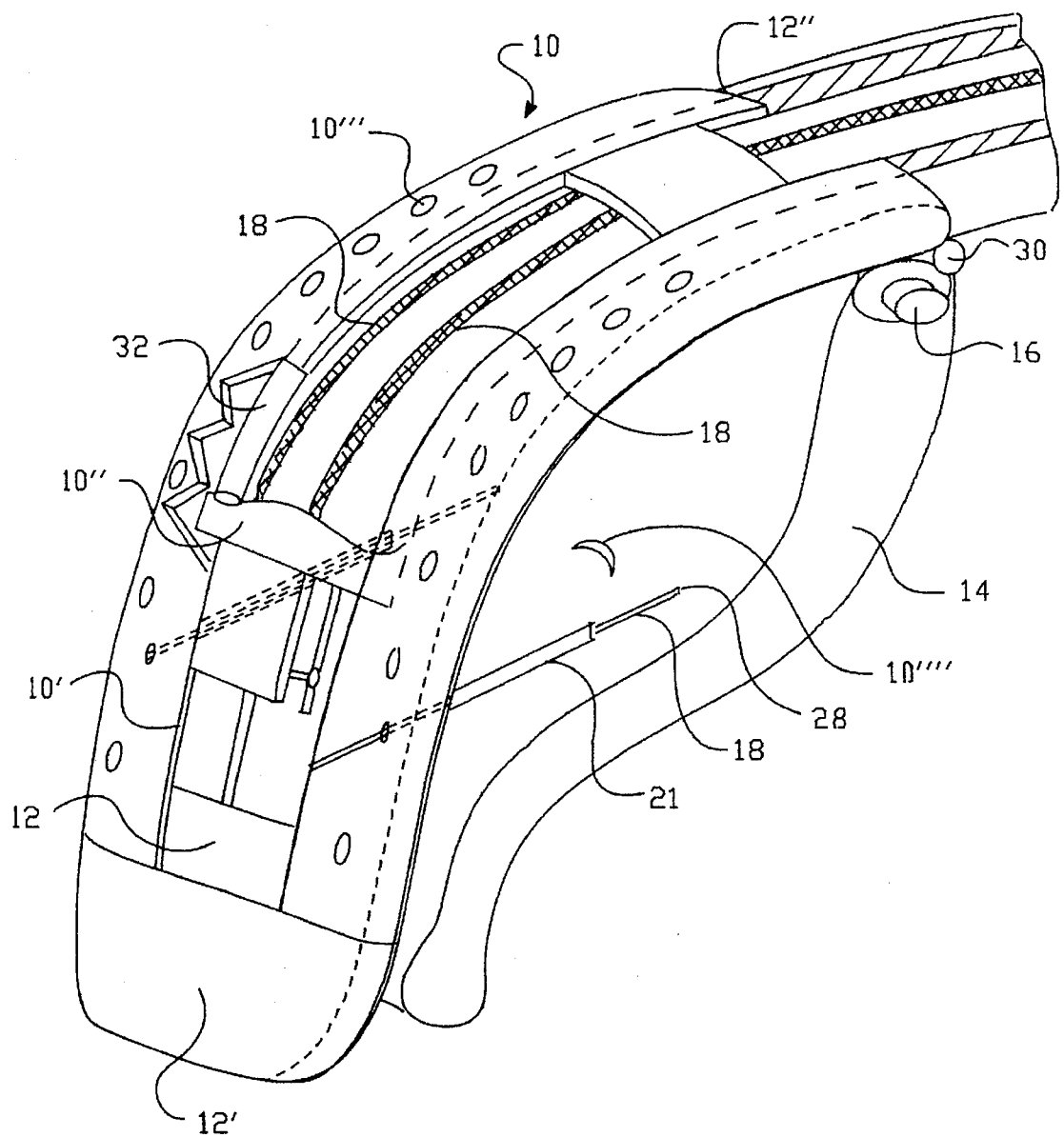
FIG. 1 is a perspective view of the apparatus for treating air way obstructions of the present invention.

Referring to FIG. 1, an apparatus for treating air way obstructions 10, is shown. Apparatus 10 is used to treat a variety of different obstructions in the body where passage of gas is restricted. One embodiment is the treatment of sleep apnea using apparatus 10 to ablate selected portions of the tongue by the use of RF, microwave, and the like. Apparatus 10 can be used to ablate targeted masses including but not limited to the tongue, tonsils, turbinates, soft palate tissues, hard tissue and mucosal tissue.

Apparatus 10 includes a first arm 12 with a distal end 12' and a proximal end 12". A second arm 14 has a distal end 14' and a proximal end 14". First arm 12 and second arm 14 are connected by a coupling device 16. Coupling device can be a ratchet hinge 16 and the like. Hinge 16 provides a coupling force that pulls arm 12 and arm 14 together. Also included are a retractor/guide rail 10', spreadable slide block 10", local cooling ports 10''' and ultrasound imager or transducers 10''''.

Figure 2:
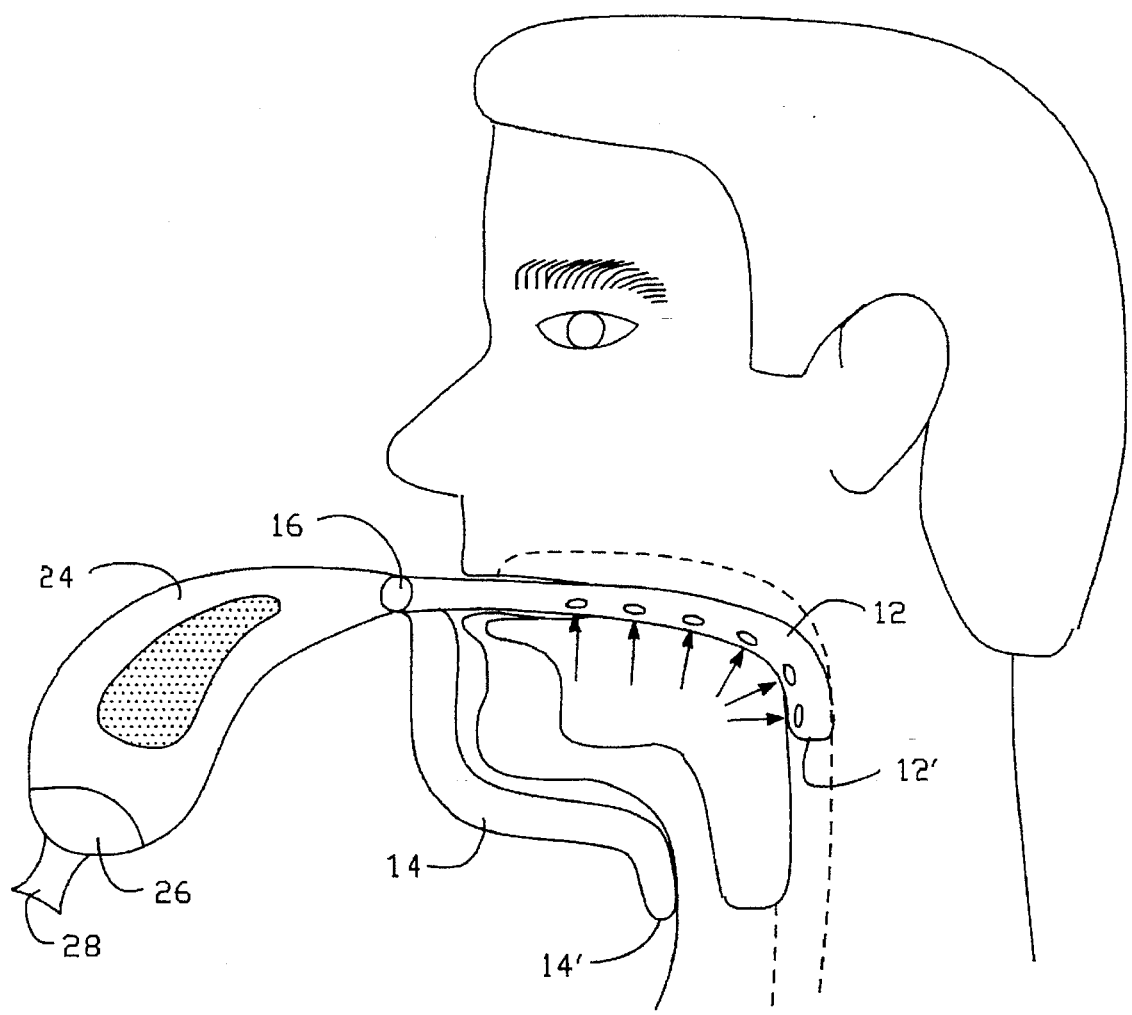
FIG. 2 is a cross-sectional view of the apparatus of FIG. 1 as it is positioned around a patient's jaw and behind the tongue.

As shown in FIG. 2, arm 12 is adapted to be inserted into a patient's throat. Distal end 12' is then positioned in an adjacent relationship to a back surface of the tongue and in certain embodiments presses up against the tongue. Distal end 14' is positioned under the jaw. When so positioned, hinge 16 causes distal end 12' to be in intimate contact with the back of the tongue. Similarly, hinge 16 pushes distal end 14' against the bottom portion of the jaw. Apparatus 10 is then positioned to provide a controlled ablation of the back of the tongue, without damage to sensitive structures such as nerves, and the bottom portion of the tongue.

Figure 3:
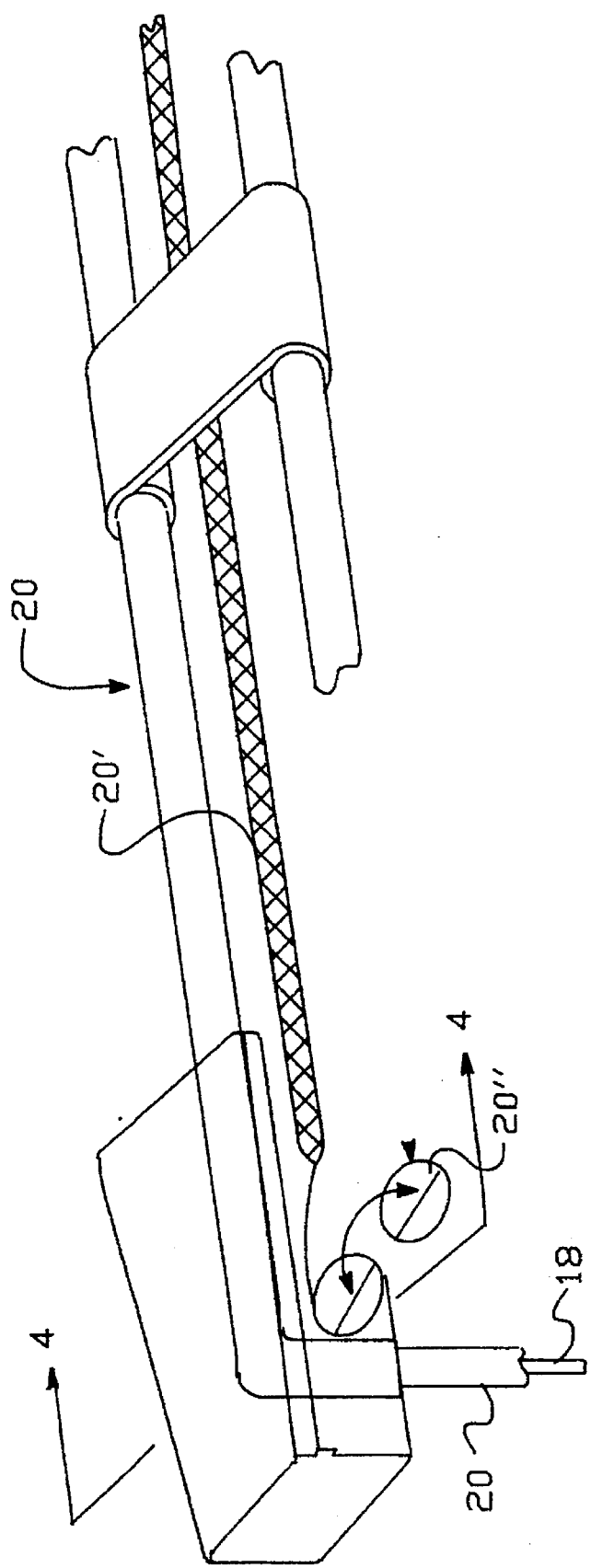
FIG. 3 is a perspective view of an electrode deployment device suitable for use with the present invention.
Figure 4:
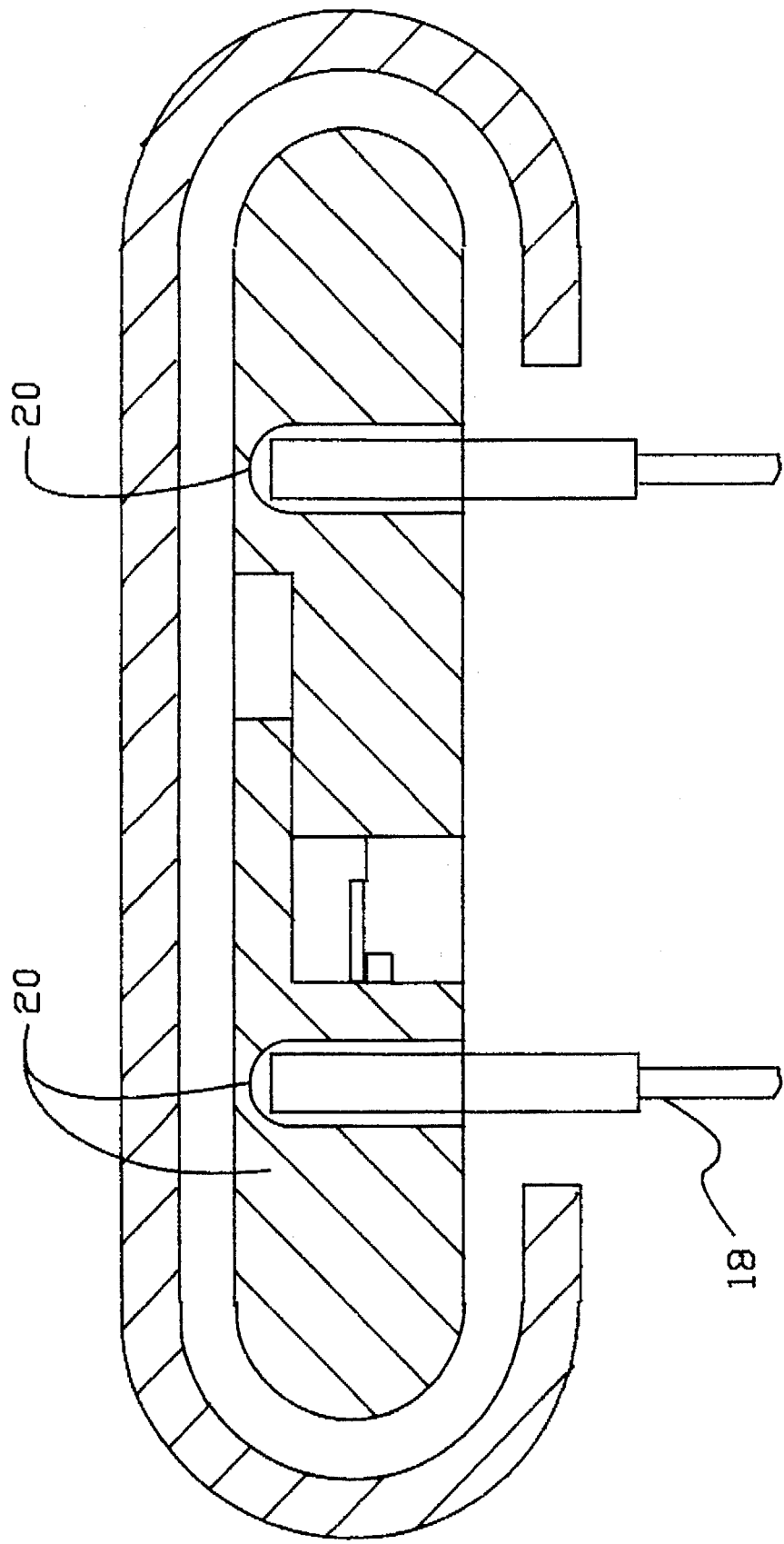
FIG. 4 is a cross-sectional view of the electrode deployment device of FIG. 3 taken along the lines 4—4.

Referring again to FIG. 1, one or more RF electrodes 18 extend from proximal end 12" to distal end 12'. RF electrodes 18 extend through the body of first arm 12, or alternatively, can extend through lumens formed in the body of first arm 12. As shown in FIGS. 3 and 4, RF electrodes 18 are advanced and retracted in and out of the tongue with an electrode deployment device 20. Suitable deployment devices 20 include but are not limited to mechanical pull cables 20', a spreader/roller 20", which advance and retract RF electrodes 18 in and out of the targeted ablation mass, such as the tongue.

Second arm 14 can also include one or more RF electrodes 18. These electrodes are advanced and retracted in and out of the bottom portion of the tongue. The same or a suitable deployment device 20 is coupled to this set of RF electrodes 18. RF electrodes 18 can be operated in bipolar or monopolar modes.

Figure 5:
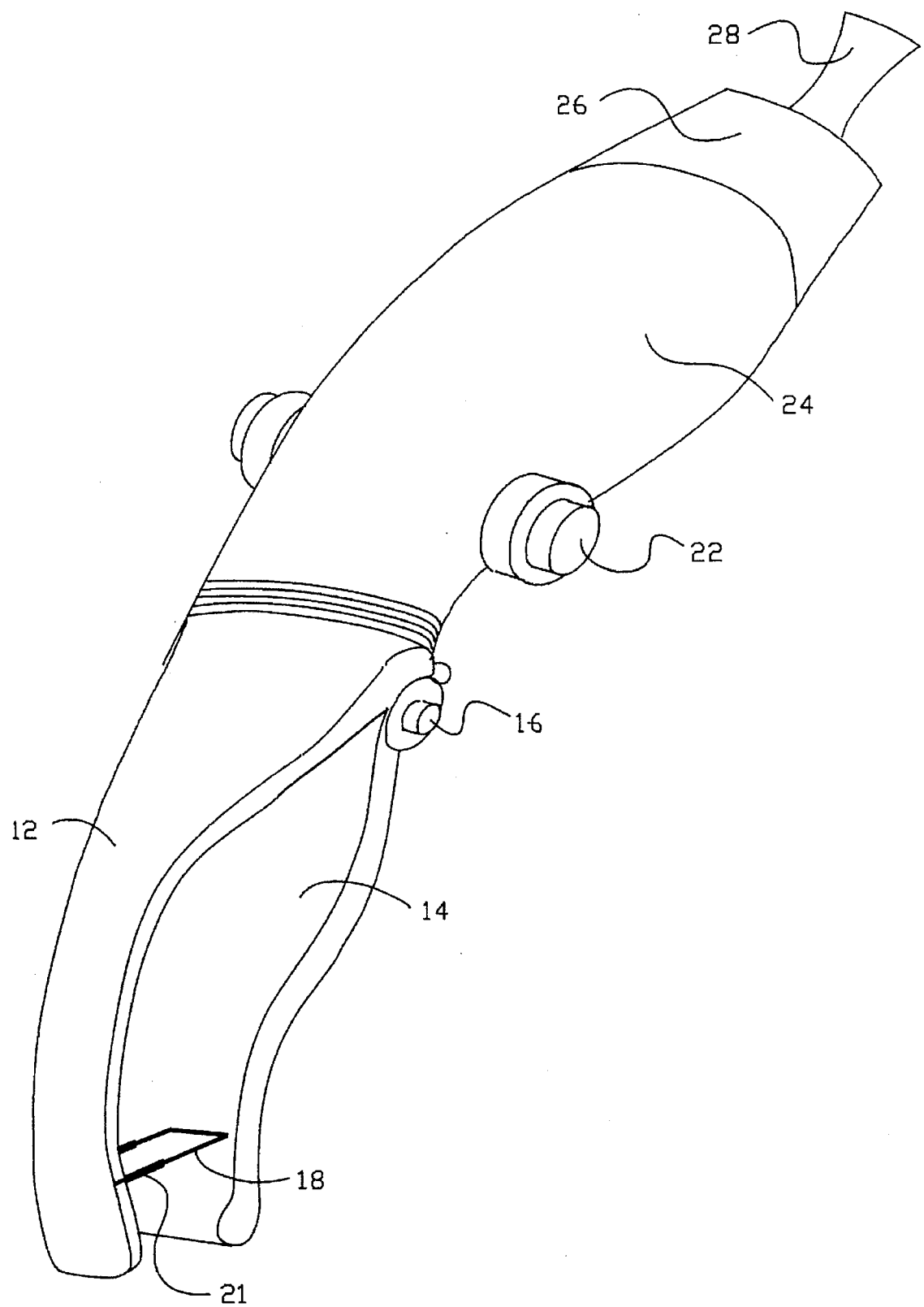
FIG. 5 is a perspective view of the apparatus of FIG. 1 including a handle.

Referring to FIG. 5, each RF electrode 18 has a insulation sleeve 21 slideably positioned around its exterior. A suitable insulation material is polyimide. Insulation sleeves 21 are advanced and retracted along an exterior longitudinal surface of RF electrodes 18 and define an ablation surface which delivers RF energy to the tongue or other desired tissue site. Coupled with insulation sleeves 21 is one or more insulation sleeve advancement and retraction actuators 22.

First and second arm proximal ends 12" and 14" are coupled to a handle 24. A visualization apparatus 26, with or without eyepiece, can be coupled to handle 24.

As shown in FIG. 1, one or more sensors 28 are positioned in an interior or exterior of RF electrodes 18, or at a surface of first and second arms 12 and 14. Sensors 28 permit accurate measurement of temperature or impedance at a tissue site in order to determine, (i) the extent of ablation, (ii) the amount of ablation, (iii) whether or not further ablation is needed, (iv) the boundary or periphery of the ablated mass and (v) prevents non-targeted tissue from being destroyed or ablated.

Sensors 28 are of conventional design, including but not limited to thermistors thermocouple, resistive wires, and the like. Suitable thermal sensors 28 include a T type thermocouple with copper constantene, J type, E type, K type, thermistors, fiber optics, resistive wires, thermocouple IR detectors, and the like. It will be appreciated that sensors 28 need not be thermal sensors.

Sensors 28 measure temperature and/or impedance to permit monitoring and a desired level of ablation to be achieved without destroying too much tissue. This reduces damage to tissue surrounding the targeted mass to be ablated. By monitoring the temperature at various points within the interior of the selected mass, a determination can be made when ablation is complete. If at any time sensor 28 determines that a desired ablation temperature is exceeded, then an appropriate feedback signal is received at an energy source which then regulates the amount of energy delivered to RF electrodes 18.

Thus the geometry of the ablated mass is selectable and controllable. Any number of different ablation geometries can be achieved.

An air or oxygen lumen 30 is included in first arm 12 and extends from proximal end 12" to distal end 12'. Lumen 30 provides air flow to the lungs during the ablation procedure. Any number of different lumens can also be incorporated into first or second arm 12 or 14. For example, in certain embodiments it may be desirable to include an anesthesia lumen 32 that is coupled to an anesthesia source. Further, a multiplexer can be coupled to RF electrodes 18 to provide ablation at different sites and at different time periods for varying lengths of time.

Resources, which can be hardware, soilware, or a combination of both, are connected with sensors 28, electrodes 18 and energy source 34 to provide an output for delivering and maintaining a selected energy at electrodes 18. Further, the resources provides an output that maintains a selected energy at primary and secondary antennas for a selected length of time.

The following discussion pertains particularly to the use of an RF energy source 34 and RF electrodes 18. It will be appreciated that devices similar to those associated with RF electrode 18 can be utilized with laser optical fibers, microwave devices and the like.

Figure 6:
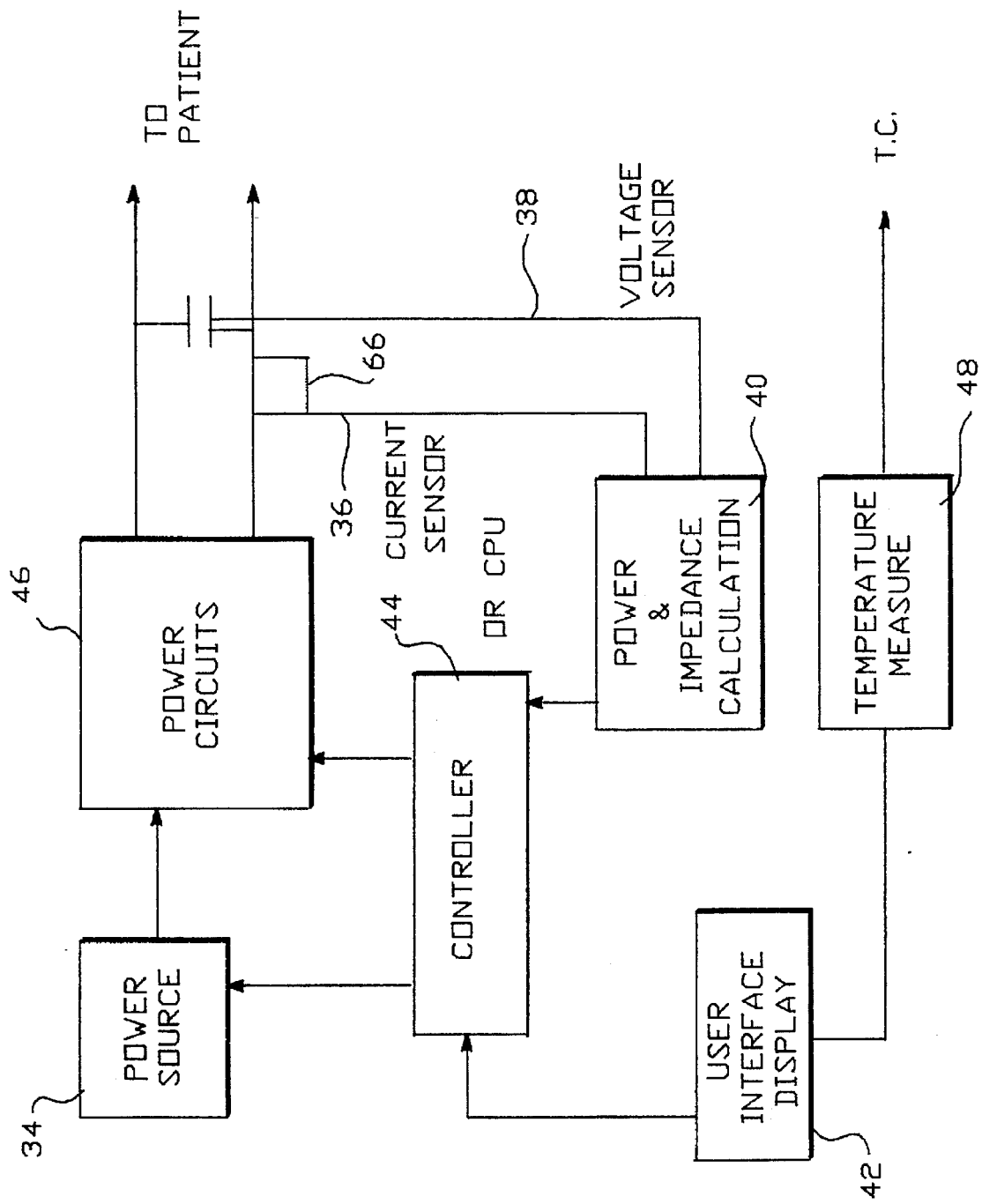
FIG. 6 is a block diagram of the electronics of the temperature feedback device of the present invention.

Referring now to FIG. 6, a sensor feed apparatus is coupled to sensors 28 maintains a tissue adjacent to RF electrodes 18 at a desired temperature for a selected period of time. Each RF electrode 18 is connected to resources which generate an independent output for each RF electrode 18. Further, the resources provides an output that maintains a selected energy at RF electrodes for a selected length of time.

Current delivered through RF electrodes 18 is measured by current sensor 36. Voltage is measured by voltage sensor 38. Impedance and power are then calculated at power and impedance calculation device 40. These values can then be displayed at user interface and display 42. Signals representative of power and impedance values are received by controller 44.

A control signal is generated by controller 44 that is proportional to the difference between an actual measured value, and a desired value. The control signal is used by power circuits 46 to adjust the power output in an appropriate amount in order to maintain the desired power delivered at the respective RF electrodes.

In a similar manner, temperatures detected at sensors 28 provide feedback for maintaining a selected power. The actual temperatures are measured at temperature measurement device 48, and the temperatures are displayed at user interface and display 42. A control signal is generated by controller 44 that is proportional to the difference between an actual measured temperature, and a desired temperature. The control signal is used by power circuits 46 to adjust the power output in an appropriate amount in order to maintain the desired temperature delivered at the respective sensor. A multiplexer can be included to measure current, voltage and temperature, at the numerous sensors 28, and energy can be delivered to RF electrodes in monopolar or bipolar fashion.

Controller 44 can be a digital or analog controller, or a computer with software. When controller 44 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 42 includes operator controls and a display. Controller 44 can be coupled to imaging systems, including but not limited to ultrasound, CT scanners, X-ray, MRI, mammographic X-ray and the like. Further, direct visualization and tactile imaging can be utilized.

The output of current sensor 36 and voltage sensor 38 is used by controller 44 to maintain a selected power level at RF electrodes 18. The amount of RF energy delivered controls the amount of power. A profile of power delivered can be incorporated in controller 44, and a preset amount of energy to be delivered can also be profiled.

Circuitry, software and feedback to controller 44 result in process control, and the maintenance of the selected power that is independent of changes in voltage or current, and are used to change, (i) the selected power, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 28.

Figure 7:
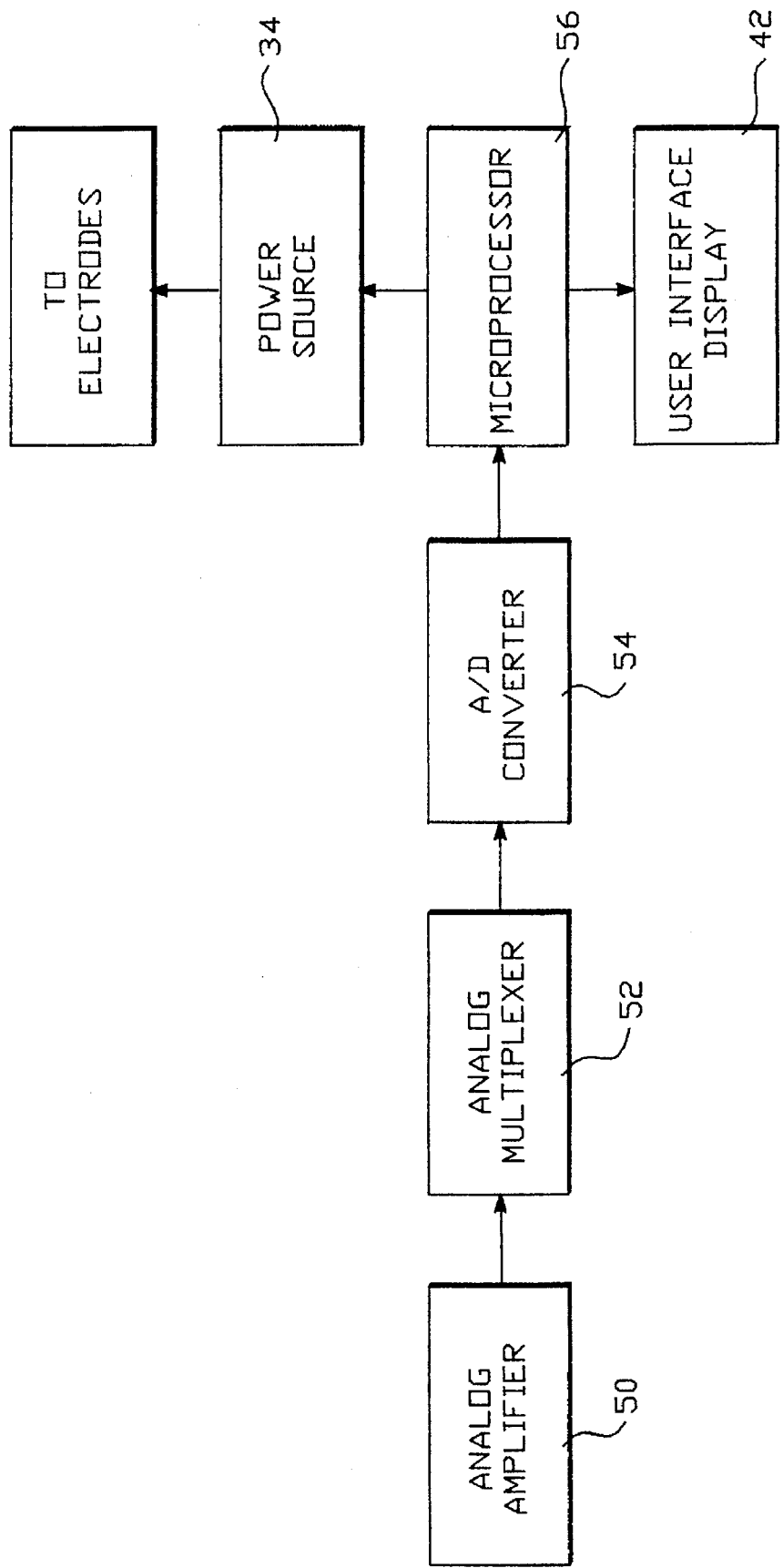
FIG. 7 illustrates a block diagram illustrating the incorporation of a microprocessor.

Referring now to FIG. 7, current sensor 36 and voltage sensor 38 are connected to the input of an analog amplifier 50. Analog amplifier 50 can be a conventional differential amplifier circuit for use with sensors 28. The output of analog amplifier 50 is sequentially connected by an analog multiplexer 52 to the input of A/D converter 54. The output of analog amplifier 50 is a voltage which represents the respective sensed temperatures. Digitized amplifier output voltages are supplied by A/D converter 54 to a microprocessor 56. Microprocessor 56 may be a type 68HCII available from Motorola. However, it will be appreciated that any suitable microprocessor or general purpose digital or analog computer can be used to calculate impedance or temperature.

Microprocessor 56 sequentially receives and stores digital representations of impedance and temperature. Each digital value received by microprocessor 56 corresponds to different temperatures and impedances.

Calculated power and impedance values can be indicated on user interlace and display 42. Alternatively, or in addition to the numerical indication of power or impedance, calculated impedance and power values can be compared by microprocessor 56 with power and impedance limits. When the values exceed predetermined power or impedance values, a warning can be given on user interface and display 42, and additionally, the delivery of RF energy can be reduced, modified or interrupted. A control signal from microprocessor 56 can modify the power level supplied by power source 58.

Figure 8:
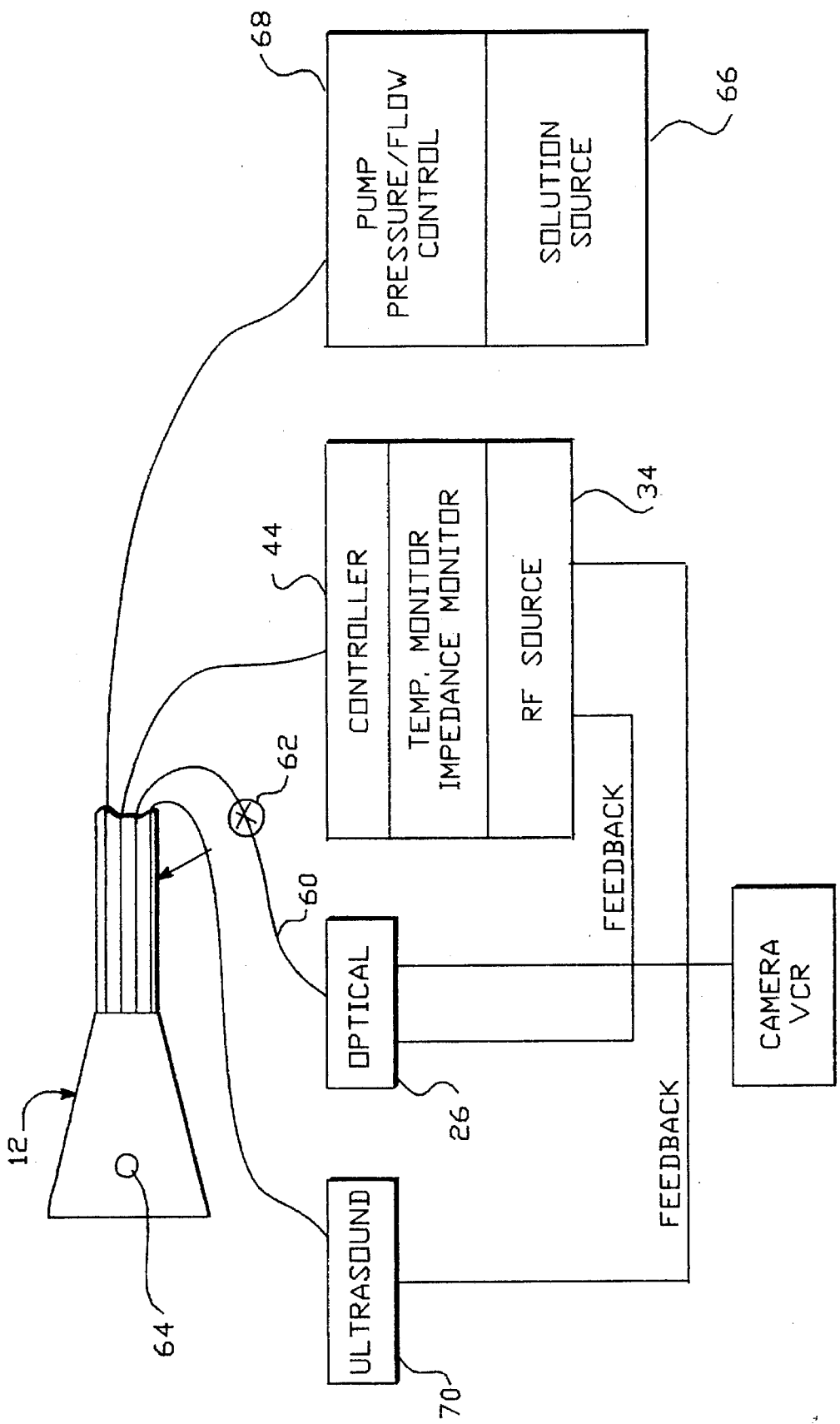
FIG. 8 is a schematic diagram illustrating the relationship of the device of FIG. 1 with ultrasound, optical, energy source and solution sources.

Referring now to FIG. 8, visualization apparatus 26 can include a light source, associated illumination and imaging fibers 60, which can be in the form of a flexible endoscope, and associated switch 62 that operates the rotation and viewing of viewing optics 64. Visualization apparatus 26 can also include an output going to a VCR, camera, and the like, and a feedback output to energy source 34 and controller 44. Energy source 34 can incorporate a controller, as well as both temperature and impedance monitoring devices. Infusion medium source 66 can include a pump/pressure flow control device 68, as is well known to those skilled in the art. An ultrasound source 70 is coupled to one or more ultrasound transducers 10"" that are positioned in or on the tongue. An output is associated with ultrasound source 70 and energy source 34.

Each ultrasound transducer 10"" can include a piezoelectric crystal mounted on a backing material. The piezoelectric crystal is connected by electrical leads to ultrasound power source 72. Each ultrasound transducer 10"" transmits ultrasound energy into adjacent tissue, such as the tongue. Ultrasound transducers 10"" can be in the form of an imaging probe such as Model 21362, manufactured and sold by Hewlett Packard Company.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An apparatus for treating air way obstructions, comprising:
    a first arm including a proximal end and a distal end, the first arm distal end being insertable into an oral cavity and adapted to be positioned adjacent to a surface of a tongue;
    a second arm including a proximal end and a distal end, the second arm being adapted to be positioned under a jaw;
    a coupling member mechanically coupling the first arm with the second arm permitting rotational movement of each arm about a longitudinal axis of the coupling member; and
    a plurality of RF electrodes at least partially positioned in the first arm and adapted to be configured to be precisely positioned through a selected surface of the tongue into an interior of the tongue and adapted to be retracted out of the tongue and into the first arm.

2. The apparatus of claim 1, further comprising:
    a plurality of insulation sleeves, each insulation sleeve being associated with an RF electrode and slideably positioned around an exterior of the RF electrode to define an RF ablation surface.

3. The apparatus of claim 1, further comprising:
    a second plurality of RF electrodes at least partially positioned in the second arm and adapted to be configured to be precisely positioned through a selected undersurface of the tongue into an interior of the tongue.

4. The apparatus of claim 3, further comprising:
    a plurality of insulation sleeves, each insulation sleeve being associated with an RF electrode positioned in the second arm and slideably positioned around an exterior of the RF electrode to define an RF ablation surface.

5. The apparatus of claim 1, further comprising:
    a handle coupled to the first and second arms.

6. The apparatus of claim 1, further comprising:
    a plurality of sensors associated with the plurality of RF electrodes positioned in the first arm.

7. The apparatus of claim 1, further comprising:
    a visualization apparatus coupled to one of the first or second arms.

8. The apparatus of claim 1, further comprising:
    a plurality of sensors positioned on an exterior surface of the distal end of the first arm to measure a temperature of the back of the tongue.

9. The apparatus of claim 1, further comprising:
    a lumen extending through the first arm providing an introduction of oxygen into a patient.

10. The apparatus of claim 1, further comprising:
    an anesthetic lumen extending through the first arm providing injection of an anesthetic at the first arm distal end.

11. The apparatus of claim 1, wherein the coupling member is a hinge.

12. The apparatus of claim 1, wherein the coupling member applies a compression force to the first and second arms.

13. An apparatus for treating air way obstructions, comprising:
    a first arm including a proximal end and a distal end, the first arm distal end being adapted to be insertable into an oral cavity and adapted to be positioned adjacent to a surface of the tongue;
    a second arm including a proximal end and a distal end, the second arm being adapted to be positioned under the jaw;
    a coupling member coupling the first arm with the second arm permitting rotational movement of each arm about a longitudinal axis of the coupling member;
    a plurality of RF electrodes at least partially positioned in the first arm and adapted to be configured to be precisely positioned through a selected surface of the tongue into an interior of the tongue and adapted to be retracted out of the tongue and into the first arm;
    one or more sensors positioned at one of an interior or an exterior of the RF electrodes or on an interior or exterior surface of the first arm distal end, to detect one of impedance or temperature; and
    a sensor feedback apparatus coupled to the sensors for maintaining a tissue adjacent to the RF electrodes at a desired temperature.

14. The apparatus of claim 13, wherein each of the RF electrodes is independently connected to the resources, and the resources generates an independent output for each RF electrode.

15. The apparatus of claim 13, wherein hardware and/or software alone or in combination provides an output that maintains a selected energy at an RF antennae for a selected length of time.

16. The apparatus of claim 13, wherein the apparatus operates in a mono-polar mode.

17. The apparatus of claim 13, wherein the apparatus operates in a bipolar mode.

18. The apparatus of claim 13, further comprising:
    a multiplexer coupled to the plurality of RF electrodes.

19. The apparatus of claim 13, further comprising:
    a plurality of insulation sleeves, each insulation sleeve being associated with an RF electrode and slideably positioned around an exterior of the RF electrode to define an RF ablation surface.

20. The apparatus of claim 13, further comprising:
    a second plurality of RF electrodes at least partially positioned in the second arm and configured to be precisely positioned through a selected undersurface surface of the tongue into an interior of the tongue.

21. The apparatus of claim 20, further comprising:
    a plurality of insulation sleeves, each insulation sleeve being associated with an RF electrode positioned in the second arm and slideably positioned around an exterior of the RF electrode to define an RF ablation surface.

22. The apparatus of claim 13, further comprising:
    a handle coupled to the first and second arms.

23. The apparatus of claim 13, further comprising:
    a visualization apparatus coupled to one of the first or second arms.

24. The apparatus of claim 13, further comprising:
a lumen extending through the first arm providing an introduction of oxygen into a patient.

25. The apparatus of claim 13, further comprising:
an anesthetic lumen extending through the first arm providing injection of an anesthetic at the first arm distal end.

26. The apparatus of claim 13, wherein the coupling member is a hinge.

27. The apparatus of claim 13, wherein the coupling member applies a compression force to the first and second arms.

* * * * *